US005985662A

United States Patent [19]
Anderson et al.

[11] Patent Number: 5,985,662
[45] Date of Patent: Nov. 16, 1999

[54] ANTISENSE INHIBITION OF HEPATITIS B VIRUS REPLICATION

[75] Inventors: Kevin P. Anderson; Lex M. Cowsert, both of Carlsbad, Calif.

[73] Assignee: Isis Pharmaceuticals Inc., Carlsbad, Calif.

[21] Appl. No.: 08/501,968

[22] Filed: Jul. 13, 1995

[51] Int. Cl.$^6$ ............... C12N 5/08; C12N 7/06; C07H 21/00; C07H 21/04
[52] U.S. Cl. .......................... 435/375; 536/24.5
[58] Field of Search ................... 435/6, 91.1, 240.2, 435/238, 375; 514/44; 536/23.1, 24.3, 24.5

[56] References Cited

U.S. PATENT DOCUMENTS

| | | | |
|---|---|---|---|
| 4,806,463 | 2/1989 | Goodchild et al. | 435/5 |
| 5,004,810 | 4/1991 | Draper | 536/24.5 |
| 5,166,195 | 11/1992 | Ecker | 514/44 |
| 5,194,428 | 3/1993 | Agrawal et al. | 514/44 |
| 5,264,423 | 11/1993 | Cohen et al. | 514/44 |
| 5,276,019 | 1/1994 | Cohen et al. | 514/44 |
| 5,646,262 | 7/1997 | Korba et al. | 536/24.5 |
| 5,728,518 | 3/1998 | Carmichael | 435/5 |

FOREIGN PATENT DOCUMENTS

| | | |
|---|---|---|
| 90/13667 | 11/1990 | WIPO. |
| 93/13120 | 8/1993 | WIPO. |
| 94/24864 | 11/1994 | WIPO. |
| 95/02690 | 1/1995 | WIPO. |

OTHER PUBLICATIONS

Gura et al. "Antisense has Growing Pains" Science 270: 575–577, Oct. 1995.

Stull et al. "Antigene, Ribozyme, andd Aptamer Nucleic Acid Drugs: Prospect and Progress" Pharmaceutical Res. 12(4): 465–481, Apr. 1995.

Whitton "Antisense treatment of Viral Infection" Adv. Virus Res. 44: 267–303, 1994.

Zon et al. in "Oligonucleotides and Analogues: A Practical Approach" F. Eckstein, ed. IRL Press, New York, pp. 87–108, 1991.

*Current Protocols in Molecular Biology*, Frederick M. Ausubel et al., eds., John Wiley & Sons Inc., 1994, Section 2.9B.

Blum et al., "Inhibition of hepatitis B. virsu by antisense oligodeoxynucleotides", *Lancet* 1991, 337, 1230.

Cornelius, C.E., 1988, in *The Liver: Biology and Pathobiology*, Second Ed. I.M. Arias et al., eds. Raven Press, Ltd., N.Y., pp. 1315–1336.

Junker–Niepmann et al., "A short cis–acting sequence is required for hepatitis B virus pregenome encapsidation and sufficient for packaging of foreign RNA", *EMBO J*. 1990, 10, 3389–3396.

Korba and Gerin, "Use of standardized cell culture assay to assess activities of nucleoside analogs against hepatitis B virus replication", *Antiviral Res*. 1992, 19, 55–70.

Korba and Milman, "A cell culture assay for compounds which inhibit hepatitis B virus replication", *Antiviral Res*. 1991, 15, 217–228.

Gerin, J.L. 1984. In *Advances in Hepatitis Research*, F. Chisari, ed. Masson Publishing USA, Inc. New York, pp. 40–48.

Gerin et al. 1986 In *Vaccines 86: New approaches to Immunization.*, F. Brown et al., eds. Cold Spring Harbor Laboratory Press, N.Y., pp. 383–386.

Goodarzi et al., "Antisense oligodeoxyribonucleotides inhibit the expression of the gene for hepatitis B virus surface antigen", *J. Gen. Virol*. 1990, 71, 3021–3025.

Miller and Robinson, "Common evolutionary origin of hepatitis B virus and retroviruses", *Proc. Natl. Acad. Sci*. 1986, 83, 2531–2535.

Offensperger et al., "In vivo inhibition of duck hepatitis B virus replication and gene expression by phosphorothioate modified antisense oligodeoxynucleotides", *EMBO J*. 1993, 12, 1257–1262.

Sambrook et al., 1989, *Molecular Cloning: A Laboratory Manual*, Cold Spring Harbor, NY, pp. 7.53–7.55 and pp. 9.31–9.58.

Maister, Philippa,"Isis' Antisense Drug Shows Promise for Retinitis", *BioWorld Today*, Apr. 29, 1994, p. 3.

Takahashi et al., "Acute hepatitis in rats expressing human hepatitis B virus transgenes", *Proc. Natl. Acad. Sci. U.S.A*. 1995, 92, 1470–1474.

Tennant, B.C. and J.L. Gerin. 1994. In *The Liver: Biology and Pathobiology*, Third Edition. I.M. Arias et al., eds. Raven Press, Ltd., N.Y. pp. 1455–1466.

Yao et al., *Chung Hua I Hsueh Tsa Chih* 1994, 74, 74–76.

Wu and Wu, "Specific Inhibition of Hepatitis B Viral Gene Expression in Vitro by Targeted Antisense Oligonucleotides", *J. Biol. Chem*. 1992, 267, 12436–12439.

*Primary Examiner*—Nancy Degen
*Assistant Examiner*—Thomas G. Larson
*Attorney, Agent, or Firm*—Law Offices of Jane Massey Licata

[57] ABSTRACT

Antisense oligonucleotides are provided which are capable of inhibiting HBV replication. These oligonucleotides are specifically hybridizable with HBV RNAs which encode a P gene product, S gene product or C gene product, or with the 5' cap region, U5 region, $\epsilon$ region or translation initiation site of HBV RNA. Methods of diagnosing HBV infection, methods of inhibiting HBV replication, methods of treating an HBV infection and methods of treating or preventing HBV-associated diseases using the oligonucleotides of the invention are also provided. Such diseases may include acute hepatitis, chronic hepatitis, fulminant hepatitis, or hepatocellular carcinoma.

2 Claims, No Drawings

SEQUENCE LISTING (1) GENERAL INFORMATION:

(iii) NUMBER OF SEQUENCES: 40

(2) INFORMATION FOR SEQ ID NO: 1:

(i) SEQUENCE CHARACTERISTICS:
       (A) LENGTH: 21 nucleotides
       (B) TYPE: nucleic acid
       (C) STRANDEDNESS: single
       (D) TOPOLOGY: linear (iii) HYPOTHETICAL: NO (iv) ANTI-SENSE: YES (xi) SEQUENCE DESCRIPTION: SEQ ID NO: 1:

CCTGATGTGA TGTTCTCCAT G                                            21

(2) INFORMATION FOR SEQ ID NO: 2:

(i) SEQUENCE CHARACTERISTICS:
       (A) LENGTH:  20 nucleotides
       (B) TYPE: nucleic acid
       (C) STRANDEDNESS: single
       (D) TOPOLOGY: linear (iii) HYPOTHETICAL: NO (iv) ANTI-SENSE: YES (xi) SEQUENCE DESCRIPTION: SEQ ID NO: 2:

GAACTGGAGC CACCAGCAGG                                              20

(2) INFORMATION FOR SEQ ID NO: 3:

(i) SEQUENCE CHARACTERISTICS:
       (A) LENGTH:  19 nucleotides
       (B) TYPE: nucleic acid
       (C) STRANDEDNESS: single
       (D) TOPOLOGY: linear (iii) HYPOTHETICAL: NO (iv) ANTI-SENSE: YES (xi) SEQUENCE DESCRIPTION: SEQ ID NO: 3:

GAAAGATTCG TCCCCATGC                                               19

(2) INFORMATION FOR SEQ ID NO: 4:

(i) SEQUENCE CHARACTERISTICS:
       (A) LENGTH:  21 nucleotides
       (B) TYPE: nucleic acid
       (C) STRANDEDNESS: single
       (D) TOPOLOGY: linear (iii) HYPOTHETICAL: NO (iv) ANTI-SENSE: YES (xi) SEQUENCE DESCRIPTION: SEQ ID NO: 4:

CCACTGCATG GCCTGAGGAT G                                            21

(2) INFORMATION FOR SEQ ID NO: 5:

(i) SEQUENCE CHARACTERISTICS:
       (A) LENGTH:  21 nucleotides (B) TYPE: nucleic acid
            (C) STRANDEDNESS: single
            (D) TOPOLOGY: linear (iii) HYPOTHETICAL: NO (iv) ANTI-SENSE: YES (xi) SEQUENCE DESCRIPTION: SEQ ID NO: 5:

TAGGCAGAGG TGAAAAAGTT G                                              21

(2) INFORMATION FOR SEQ ID NO: 6:

(i) SEQUENCE CHARACTERISTICS:
            (A) LENGTH:  21 nucleotides
            (B) TYPE: nucleic acid
            (C) STRANDEDNESS: single
            (D) TOPOLOGY: linear (iii) HYPOTHETICAL: NO (iv) ANTI-SENSE: YES (xi) SEQUENCE DESCRIPTION: SEQ ID NO: 6:

ACAGCTTGGA GGCTTGAACA G                                              21

(2) INFORMATION FOR SEQ ID NO: 7:

(i) SEQUENCE CHARACTERISTICS:
            (A) LENGTH:  21 nucleotides
            (B) TYPE: nucleic acid
            (C) STRANDEDNESS: single
            (D) TOPOLOGY: linear (iii) HYPOTHETICAL: NO (iv) ANTI-SENSE: YES (xi) SEQUENCE DESCRIPTION: SEQ ID NO: 7:

CCAAAGCCAC CCAAGGCACA G                                              21

(2) INFORMATION FOR SEQ ID NO: 8:

(i) SEQUENCE CHARACTERISTICS:
            (A) LENGTH:  21 nucleotides
            (B) TYPE: nucleic acid
            (C) STRANDEDNESS: single
            (D) TOPOLOGY: linear (iii) HYPOTHETICAL: NO (iv) ANTI-SENSE: YES (xi) SEQUENCE DESCRIPTION: SEQ ID NO: 8:

ATGTCCATGC CCCAAAGCCA C                                              21

(2) INFORMATION FOR SEQ ID NO: 9:

(i) SEQUENCE CHARACTERISTICS:
            (A) LENGTH:  21 nucleotides
            (B) TYPE: nucleic acid
            (C) STRANDEDNESS: single
            (D) TOPOLOGY: linear (iii) HYPOTHETICAL: NO (iv) ANTI-SENSE: YES (xi) SEQUENCE DESCRIPTION: SEQ ID NO: 9:

GATAGGGGCA TTTGGTGGTC T                                              21

(2) INFORMATION FOR SEQ ID NO: 10:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 10:

GTTCCCAAGA ATATGGTGAC C                                      21

(2) INFORMATION FOR SEQ ID NO: 11:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 11:

CGGAAGTGTT GATAAGATAG G                                      21

(2) INFORMATION FOR SEQ ID NO: 12:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 12:

TGAACAGTAG GACATGAACA                                        20

(2) INFORMATION FOR SEQ ID NO: 13:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 13:

GGCTTGAACA GTAGGACATG                                        20

(2) INFORMATION FOR SEQ ID NO: 14:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 14:

TTGGAGGCTT GAACAGTAGG                                                    20

(2) INFORMATION FOR SEQ ID NO: 15:

(i) SEQUENCE CHARACTERISTICS:
            (A) LENGTH:  20 nucleotides
            (B) TYPE: nucleic acid
            (C) STRANDEDNESS: single
            (D) TOPOLOGY: linear (iii) HYPOTHETICAL: NO (iv) ANTI-SENSE: YES (xi) SEQUENCE DESCRIPTION: SEQ ID NO: 15:

ACAGCTTGGA GGCTTGAACA                                                    20

(2) INFORMATION FOR SEQ ID NO: 16:

(i) SEQUENCE CHARACTERISTICS:
            (A) LENGTH:  20 nucleotides
            (B) TYPE: nucleic acid
            (C) STRANDEDNESS: single
            (D) TOPOLOGY: linear (iii) HYPOTHETICAL: NO (iv) ANTI-SENSE: YES (xi) SEQUENCE DESCRIPTION: SEQ ID NO: 16:

AAGGCACAGC TTGGAGGCTT                                                    20

(2) INFORMATION FOR SEQ ID NO: 17:

(i) SEQUENCE CHARACTERISTICS:
            (A) LENGTH:  20 nucleotides
            (B) TYPE: nucleic acid
            (C) STRANDEDNESS: single
            (D) TOPOLOGY: linear (iii) HYPOTHETICAL: NO (iv) ANTI-SENSE: YES (xi) SEQUENCE DESCRIPTION: SEQ ID NO: 17:

CACCCAAGGC ACAGCTTGGA                                                    20

(2) INFORMATION FOR SEQ ID NO: 18:

(i) SEQUENCE CHARACTERISTICS:
            (A) LENGTH:  20 nucleotides
            (B) TYPE: nucleic acid
            (C) STRANDEDNESS: single
            (D) TOPOLOGY: linear (iii) HYPOTHETICAL: NO (iv) ANTI-SENSE: YES (xi) SEQUENCE DESCRIPTION: SEQ ID NO: 18:

AAAGCCACCC AAGGCACAGC                                                    20

(2) INFORMATION FOR SEQ ID NO: 19:

(i) SEQUENCE CHARACTERISTICS:
            (A) LENGTH:  20 nucleotides
            (B) TYPE: nucleic acid
            (C) STRANDEDNESS: single (D) TOPOLOGY: linear (iii) HYPOTHETICAL: NO (iv) ANTI-SENSE: YES (xi) SEQUENCE DESCRIPTION: SEQ ID NO: 19:

GCCCCAAAGC CACCCAAGGC                                                          20

(2) INFORMATION FOR SEQ ID NO: 20:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 20:

TCCATGCCCC AAAGCCACCC                                                          20

(2) INFORMATION FOR SEQ ID NO: 21:

(i) SEQUENCE CHARACTERISTICS:
        (A) LENGTH: 18 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 21:

GGAGGCTTGA ACAGTAGG                                                            18

(2) INFORMATION FOR SEQ ID NO: 22:

(i) SEQUENCE CHARACTERISTICS:
        (A) LENGTH: 18 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 22:

CTTGGAGGCT TGAACAGT                                                            18

(2) INFORMATION FOR SEQ ID NO: 23:

(i) SEQUENCE CHARACTERISTICS:
        (A) LENGTH: 18 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 23:

CAGCTTGGAG GCTTGAAC                                                            18

(2) INFORMATION FOR SEQ ID NO: 24:

```
    (i) SEQUENCE CHARACTERISTICS:
        (A) LENGTH:  18 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 24:

GCACAGCTTG GAGGCTTG                                                         18

(2) INFORMATION FOR SEQ ID NO: 25:

(i) SEQUENCE CHARACTERISTICS:
         (A) LENGTH:  18 nucleotides
         (B) TYPE: nucleic acid
         (C) STRANDEDNESS: single
         (D) TOPOLOGY: linear (iii) HYPOTHETICAL: NO (iv) ANTI-SENSE: YES (xi) SEQUENCE DESCRIPTION: SEQ ID NO: 25:

AGGCACAGCT TGGAGGCT                                                         18

(2) INFORMATION FOR SEQ ID NO: 26:

(i) SEQUENCE CHARACTERISTICS:
         (A) LENGTH:  18 nucleotides
         (B) TYPE: nucleic acid
         (C) STRANDEDNESS: single
         (D) TOPOLOGY: linear (iii) HYPOTHETICAL: NO (iv) ANTI-SENSE: YES (xi) SEQUENCE DESCRIPTION: SEQ ID NO: 26:

CCAAGGCACA GCTTGGAG                                                         18

(2) INFORMATION FOR SEQ ID NO: 27:

(i) SEQUENCE CHARACTERISTICS:
         (A) LENGTH:  18 nucleotides
         (B) TYPE: nucleic acid
         (C) STRANDEDNESS: single
         (D) TOPOLOGY: linear (iii) HYPOTHETICAL: NO (iv) ANTI-SENSE: YES (xi) SEQUENCE DESCRIPTION: SEQ ID NO: 27:

CACCCAAGGC ACAGCTTG                                                         18

(2) INFORMATION FOR SEQ ID NO: 28:

(i) SEQUENCE CHARACTERISTICS:
         (A) LENGTH:  18 nucleotides
         (B) TYPE: nucleic acid
         (C) STRANDEDNESS: single
         (D) TOPOLOGY: linear (iii) HYPOTHETICAL: NO (iv) ANTI-SENSE: YES (xi) SEQUENCE DESCRIPTION: SEQ ID NO: 28:
```

AGCCACCCAA GGCACAGC                                                           18

(2) INFORMATION FOR SEQ ID NO: 29:

(i) SEQUENCE CHARACTERISTICS:
        (A) LENGTH: 16 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 29:

AGGCTTGAAC AGTAGG                                                             16

(2) INFORMATION FOR SEQ ID NO: 30:

(i) SEQUENCE CHARACTERISTICS:
        (A) LENGTH: 16 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 30:

TGGAGGCTTG AACAGT                                                             16

(2) INFORMATION FOR SEQ ID NO: 31:

(i) SEQUENCE CHARACTERISTICS:
        (A) LENGTH: 16 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 31:

GCTTGGAGGC TTGAAC                                                             16

(2) INFORMATION FOR SEQ ID NO: 32:

(i) SEQUENCE CHARACTERISTICS:
        (A) LENGTH: 16 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 32:

ACAGCTTGGA GGCTTG                                                             16

(2) INFORMATION FOR SEQ ID NO: 33:

(i) SEQUENCE CHARACTERISTICS:
        (A) LENGTH: 16 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 33:

GCACAGCTTG GAGGCT                                                            16

(2) INFORMATION FOR SEQ ID NO: 34:

(i) SEQUENCE CHARACTERISTICS:
            (A) LENGTH:  16 nucleotides
            (B) TYPE: nucleic acid
            (C) STRANDEDNESS: single
            (D) TOPOLOGY: linear (iii) HYPOTHETICAL: NO (iv) ANTI-SENSE: YES (xi) SEQUENCE DESCRIPTION: SEQ ID NO: 34:

AAGGCACAGC TTGGAG                                                            16

(2) INFORMATION FOR SEQ ID NO: 35:

(i) SEQUENCE CHARACTERISTICS:
            (A) LENGTH:  16 nucleotides
            (B) TYPE: nucleic acid
            (C) STRANDEDNESS: single
            (D) TOPOLOGY: linear (iii) HYPOTHETICAL: NO (iv) ANTI-SENSE: YES (xi) SEQUENCE DESCRIPTION: SEQ ID NO: 35:

CCCAAGGCAC AGCTTG                                                            16

(2) INFORMATION FOR SEQ ID NO: 36:

(i) SEQUENCE CHARACTERISTICS:
            (A) LENGTH:  16 nucleotides
            (B) TYPE: nucleic acid
            (C) STRANDEDNESS: single
            (D) TOPOLOGY: linear (iii) HYPOTHETICAL: NO (iv) ANTI-SENSE: YES (xi) SEQUENCE DESCRIPTION: SEQ ID NO: 36:

CCACCCAAGG CACAGC                                                            16

(2) INFORMATION FOR SEQ ID NO: 37:

(i) SEQUENCE CHARACTERISTICS:
            (A) LENGTH:  16 nucleotides
            (B) TYPE: nucleic acid
            (C) STRANDEDNESS: single
            (D) TOPOLOGY: linear (iii) HYPOTHETICAL: NO (iv) ANTI-SENSE: YES (xi) SEQUENCE DESCRIPTION: SEQ ID NO: 37:

AAGCCACCCA AGGCAC                                                            16

(2) INFORMATION FOR SEQ ID NO: 38:

(i) SEQUENCE CHARACTERISTICS:

(A) LENGTH:    20 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 38:

GCCACGTACA CTGACAGCGA                                                              20

(2) INFORMATION FOR SEQ ID NO: 39:

(i) SEQUENCE CHARACTERISTICS:
        (A) LENGTH:    20 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 39:

CATCCAAGGC ACAGCTTGGA                                                              20

(2) INFORMATION FOR SEQ ID NO: 40:

(i) SEQUENCE CHARACTERISTICS:
        (A) LENGTH:    16 nucleotides
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO: 40:

AAAGCCATCC AAGGCA                                                                  16

ANTISENSE INHIBITION OF HEPATITIS B VIRUS REPLICATION

BACKGROUND OF THE INVENTION

Hepatitis B virus (HBV) is the etiological agent of a wide spectrum of clinical abnormalities and is a major public health problem worldwide. The spectrum of disease associated with HBV includes acute self-limiting infections, life-threatening fulminant hepatitis, and chronic hepatitis which can progress to cirrhosis and lead to liver failure. Furthermore, chronic infection has been epidemiologically associated with development of hepatocellular carcinoma. In areas such as Southeast Asia, China and sub-Saharan Africa where HBV infection is endemic, the proportion of chronically infected individuals may range from 5–20% of the adult population. The number of chronically infected HBV carriers worldwide has been estimated to be 200 million. The risk to these individuals of developing hepatocellular carcinoma has been estimated to be as high as 15%. Long-term consequences of HBV infection can lead to mortality in 60% of infected individuals in some populations.

Therapy for acute or chronic HBV infections is currently inadequate and has mainly been limited to supportive therapy. Experimental therapies using antiviral drugs such as adenosine arabinoside (araA) and interferon-a have proven effective in suppressing HBV replication in chronically infected individuals. However, permanent suppression after discontinuation of antiviral therapy occurs in only a small percentage of treated patients. Significant clinical benefits require an anti-HBV drug which could be administered continuously without side effects or which could eliminate HBV replication permanently following a course of therapy. An obvious need exists for a clinically effective antiviral therapy for acute and chronic HBV infections. Such an antiviral would also be useful for treating individuals accidently exposed to clinical specimens or blood products containing infectious HBV, to prevent the development of HBV-associated disease. There is also a need for research reagents and diagnostics which are able to differentiate HBV from other agents causing hepatitis and which are useful in designing appropriate therapeutic regimes.

Antisense oligonucleotides

Oligonucleotides are commonly used as research reagents and diagnostics. For example, antisense oligonucleotides, which, by nature, are able to inhibit gene expression with exquisite specificity, are often used by those of ordinary skill to elucidate the function of particular genes, for example to determine which viral genes are essential for replication, or to distinguish between the functions of various members of a biological pathway. This specific inhibitory effect has, therefore, been harnessed for research use. This specificity and sensitivity is also harnessed by those of skill in the art for diagnostic uses. Viruses capable of causing similar hepatic symptoms can be easily and readily distinguished in patient samples, allowing proper treatment to be implemented. Antisense oligonucleotide inhibition of viral replication in vitro is useful as a means to determine a proper course of therapeutic treatment. For example, before a patient suspected of having an HBV infection is treated with an oligonucleotide composition of the present invention, cells, tissues or a bodily fluid from the patient can be contacted with the oligonucleotide and inhibition of viral replication can be assayed. Effective in vitro inhibition of HBV replication indicates that the infection will be responsive to the oligonucleotide treatment.

Oligonucleotides have been employed as drugs for the treatment of disease states in animals and man. For example, workers in the field have now identified antisense, triplex and other oligonucleotide compositions which are capable of modulating expression of genes implicated in viral, fungal and metabolic diseases.

As examples, U.S. Pat. No. 5,166,195 issued Nov. 24, 1992 provides oligonucleotide inhibitors of HIV. U.S. Pat. No. 5,004,810, issued Apr. 2, 1991, provides oligomers capable of hybridizing to herpes simplex virus Vmw65 mRNA and inhibiting replication. U.S. Pat. No. 5,194,428, issued Mar. 16, 1993, provides antisense oligonucleotides having antiviral activity against influenzavirus. U.S. Pat. No. 4,806,463, issued Feb. 21, 1989, provides antisense oligonucleotides and methods using them to inhibit HTLV-III replication. U.S. Pat. No. 5,276,019 and U.S. Pat. No. 5,264,423 (Cohen et al.) are directed to phosphorothioate oligonucleotide analogs used to prevent replication of foreign nucleic acids in cells. Antisense oligonucleotides have been safely administered to humans and clinical trials of several antisense oligonucleotide drugs are presently underway. The phosphorothioate oligonucleotide, ISIS 2922, has been shown to be effective against cytomegalovirus retinitis in AIDS patients, BioWorld Today, Apr. 29, 1994, p. 3. It is thus established that oligonucleotides can be useful drugs for treatment of cells and animal subjects, especially humans.

Blum et al. (Lancet 1991, 337, 1230) showed inhibition of hepatitis B virus antigens in transfected hepatocytes by an undisclosed antisense oligodeoxynucleotide which blocked HBsAg and HBeAg synthesis as well as HBV replication.

Blum et al. (PCT publication WO 94/24864) subsequently disclosed termination of hepatitis B replication by antisense oligonucleotides complementary to mRNA which is complementary to a portion of the minus strand of the viral genome which encodes the terminal protein region of the viral polymerase.

Goodarzi et al. (*J. Gen. Virol* 1990, 71, 3021–3025) tested the effects of a number of 12- to 15-mer phosphodiester oligonucleotides on the expression of the HBV HBsAg surface antigen in an HBV-infected human cell line. They found that oligonucleotides directed against the cap site and region around the initiation site were most effective, giving inhibition of up to 96% at an oligonucleotide concentration of 17.4 $\mu$M. A phosphorothioate analog of one of the most active sequences was also tested and gave 90% inhibition of HBsAg expression at a concentration of 5.8 $\mu$M.

Wu and Wu (*J. Biol. Chem.* 1992, 267,12436–12439) used a 21-mer oligodeoxynucleotide complementary to the polyadenylation signal for HBV, coupled to an asialoglycoprotein targeting moiety. In the infected cell line HepG2, treatment with oligonucleotide-asialoglycoprotein complex at an oligonucleotide concentration of 50 $\mu$M resulted in 80% inhibition of HBsAg expression after one day and an 80% decrease in HBV DNA. In the presence of uncomplexed antisense oligonucleotide at a concentration of 50 $\mu$M, HBsAg concentrations continued to rise steadily throughout the 7 days of treatment, though after three days of treatment the treated cells had 30% less antigen than controls.

Yao et al. examined the effect of antisense phosphorothioate oligodeoxynucleotides on HBsAg and HBeAg production (Yao et al., *Chung Hua I Hsueh Tsa Chih* 1994, 74, 74–76).

Offensperger et al. (*EMBO J.* 1993, 12, 1257–1262) used phosphorothioate antisense oligonucleotides to inhibit duck hepatitis B virus (DHBV) in cultured duck hepatocytes. Nine oligonucleotides were tested, of which four were targeted to the pre-S/S region, one to the start of the polymerase region and four to the pre-C/C region. All showed some activity and two, directed to the start of the pre-S region and the direct repeat (DR)II region, were particularly active. The active oligonucleotide directed to the start of the pre-S region was tested on DHBV-infected ducklings in vivo. Oligonucleotide was injected intravenously daily for ten days, after which the livers were analyzed for DHBV. All ducklings showed a nearly complete inhibition of viral replication after oligonucleotide treatment, and no hepatotoxicity was detected. Two DHBV-negative ducklings were also treated with the same oligonucleotide and subsequently infected by injection of DHBV. These ducks were found not to be infected with DHBV twelve days later, showing that the oligonucleotide treatment was able to prevent infection.

SUMMARY OF THE INVENTION

The present invention provides antisense oligonucleotides which are capable of inhibiting HBV replication. These oligonucleotides are specifically hybridizable with portions of HBV RNA which encode a P gene product, S gene product or C gene product, or with the 5' cap region, U5 region, E region or translation initiation site of HBV RNA.

Methods of diagnosing HBV infection in cells, tissues or a bodily fluid using antisense oligonucleotides capable of inhibiting HBV replication are provided. Such methods can be used to distinguish hepatitis B from other forms of hepatitis, and are useful in designing appropriate therapeutic regimes.

The present invention also comprises methods of inhibiting HBV replication by contacting HBV, or cells, tissues or a bodily fluid suspecting of containing HBV, with antisense oligonucleotides which are capable of inhibiting HBV replication. Also provided are methods of treating an HBV infection in an animal by administering to said animal a therapeutically effective amount of an antisense oligonucleotide of the invention. Methods of treating HBV-associated diseases such as acute hepatitis, chronic hepatitis, fulminant hepatitis, or hepatocellular carcinoma, and methods of preventing HBV-associated diseases are also provided.

DETAILED DESCRIPTION OF THE INVENTION

HBV replication

HBV is the prototype member of a novel class of small DNA-containing viruses referred to as Hepadnaviruses. Infectious particles contain a spherical inner core containing the viral DNA genome, a core structural polypeptide (HBcAg), and DNA polymerase and protein kinase activities. The core is surrounded by a lipid-containing envelope bearing the virus surface antigen (HBsAg) to which neutralizing antibodies are directed. It should be noted that HBV is unrelated to hepatitis C virus (HCV), the cause of non-A, non-B hepatitis. HCV is most closely related to flaviviruses and pestiviruses, and has an RNA genome approximately 9.4 kb in size. HBV and HCV have little in common except that both cause liver disease.

The genome of HBV is remarkable for its small size (3.2 kb) and unusual characteristics. The virion DNA is circular and partially double-stranded as a result of its unique replication strategy. A larger minus strand DNA is base paired to a shorter DNA strand which is the same polarity as mRNA for virus genes (plus strand). After infection of susceptible cells the shorter plus strand is elongated using the minus strand as template and the virion associated DNA polymerase. After conversion to a covalently closed circular molecule HBV DNA is transcribed into subgenomic and full-length mRNAs and a full-length pre-genomic RNA which has a terminal redundancy at its 5' and 3' ends. Through a complex set of reactions the full-length pregenomic RNA is copied into genomic DNA using a semiconservative replication strategy and virus encoded reverse transcriptase.

The very small HBV genome is organized in an extremely efficient manner. Many regions of the genome apparently fulfill multiple functions. Four genes have been identified on the HBV genome (C, S, P, and X), but the open reading frames for the encoded proteins overlap one another. The overlapping reading frames allow for coding potential which exceeds that theoretically possible for non-redundant gene expression by 50%. Despite the efficient organization of the HBV genome, the small number of HBV gene products synthesized in infected cells has limited development of classical antiviral agents aimed at inhibiting virus protein function.

In contrast, the nature of the HBV genome provides unique opportunities for development of antiviral drugs based on antisense oligonucleotide therapy. In addition, the unique replication strategy of HBV involving a single-stranded RNA replication intermediate provides the potential for direct intervention in the genome replication process by targeting functionally important elements in the HBV pregenomic RNA.

Identification of HBV targets for antisense therapy

All of the genes present on the HBV genome are believed to be critical for virus replication and therefore could serve as useful targets for antisense therapy. However, the defined catalytic functions of some make them preferred targets for antisense therapy. The P gene product is believed to be the virus DNA polymerase. Extensive homology to reverse transcriptases of some retroviruses has been noted. It is also likely that the N-terminal domain of this protein functions as a primer for minus strand DNA synthesis during genomic replication. Inhibition of synthesis of this gene would therefore be likely to significantly interfere with HBV replication.

The S gene of HBV encodes surface antigen proteins present in the envelope of HBV virions. Three variant polypeptides are encoded by the S gene. These polypeptides are identical at their C-terminus, but initiate at alternative in-frame methionine (AUG) codons within the S gene. Oligonucleotides complementary to the S domain should interfere with synthesis of all 3 S polypeptides (S, pre-S1, and pre-S2), but the pre-S1 polypeptide may be the most critical for virus replication. This polypeptide is believed to be involved in virion assembly since pre-S1 protein is only found in intact virions. The pre-S1 protein has also been implicated as being involved in virion binding to target cell receptors. It is worth noting that the coding sequences of the S gene are contained entirely within the coding sequences for the P gene. Although the proteins are translated from different messages and different reading frames within the same sequences are utilized, a single oligonucleotide may interfere with synthesis of both proteins.

The C gene encodes the major structural polypeptide of the virion core, but also encodes a pre-C protein which is necessary for accumulation of core proteins at cell membranes. The pre-C domain contains amino acid homology to trypsin-like protease catalytic sites and may have protease activity. The 3' end of the C gene overlaps the 5' end of the P gene and oligos in the overlapping region may affect synthesis of both gene products. In addition, the pre-C and C polypeptides are translated from mRNA which is indistinguishable from full-length pregenomic RNA used as a template for genome replication.

The function of the X-gene product is presumed to be important, but the role of the X-gene in virus replication has not been clearly elucidated. The X protein can activate transcription from heterologous viral and cellular promoters, but not HBV promoters. The X-gene reading frame overlaps the 3' end of the P gene and the 5' end of the C-gene so that oligonucleotides may be designed which interfere with more than one gene.

In addition to direct inhibition of expression of virus gene products, antisense oligonucleotides may also be used to interfere with virus genome replication by binding to functionally important elements in the single stranded RNA pre-genome. Examples of some critical elements which can be targeted include the 11 bp direct repeats (DR1 and DR2) and a highly conserved 60–70 bp sequence, the U5 sequence, which is homologous to the U5-LTR sequences of certain retroviruses. Miller and Robinson, Proc. Natl. Acad. Sci. 1986, 83, 2531–2535. This conserved region is coextensive with a stem-loop structure, known as the E region, which serves as the HBV encapsidation signal and is necessary and sufficient for viral RNA encapsidation. Junker-Niepmann et al. EMBO J. 1990, 10, 3389–3396. Antisense oligonucleotides complementary to any of the messenger RNA molecules listed above would also be complementary to pregenomic RNA. Therefore tri-functional oligonucleotides may be designed which would inhibit virus replication by inhibiting expression of 2 independent gene products as well as interfering in the genomic replication process by binding to pregenomic RNA.

Antisense oligonucleotides

The present invention employs oligonucleotides 8 to 50 nucleotides in length which are specifically hybridizable with hepatitis B virus RNA and are capable of inhibiting HBV replication. In preferred embodiments, oligonucleotides are targeted to the translation initiation site, 5' cap region, U5 region and ε region of HBV RNA as well as RNA sequences encoding the P, S and C gene products of HBV. This relationship between an oligonucleotide and the nucleic acid sequence to which it is targeted is commonly referred to as "antisense." "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid (RNA or DNA) from an infectious agent. In the present invention, the target is the a translation initiation site, E, U5 or 5' cap region of HBV RNA or an HBV RNA sequence encoding a P, S, or C gene product; the latter products include S, pre-S1, pre-S2, C and pre-C. The targeting process also includes determination of a site or sites within the nucleic acid sequence for the oligonucleotide interaction to occur such that the desired effect, i.e., modulation of gene expression, will result. Once the target site or sites have been identified, oligonucleotides are chosen which are sufficiently complementary to the target, i.e., hybridize sufficiently well and with sufficient specificity, to give the desired modulation.

In the context of this invention "modulationt" means either inhibition or stimulation. Inhibition of target gene expression is presently the preferred form of modulation. This modulation can be measured, in samples derived from either in vitro or in vivo (animal) systems, in ways which are routine in the art, for example by PCR, Southern blot or slot blot assay of HBV DNA levels, Northern blot assay of HBV RNA levels or Western blot or ELISA assay of protein expression as taught in the examples of the instant application. "Hybridization," in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers or polymers comprising non-naturally occurring monomers, or portions thereof, which function similarly. Such modified or substituted oligonucleotides are often preferred over native forms because of properties such as, for example, enhanced cellular uptake, increased stability in the presence of nucleases, or enhanced target affinity. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A number of modifications have also been shown to increase binding (affinity) of the oligonucleotide to its target. Affinity of an oligonucleotide for its target is routinely determined by measuring the Tm of an oligonucleotide/target pair, which is the temperature at which the oligonucleotide and target dissociate. Dissociation is detected spectrophotometrically. The higher the Tm, the greater the affinity of the oligonucleotide for the target. In some cases, oligonucleotide modifications which enhance target binding affinity are also, independently, able to enhance nuclease resistance.

Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar ("backbone") linkages. Most preferred are phosphorothioates and those with $CH_2$-NH-O-$CH_2$, $CH_2$-N($CH_3$)-O-$CH_2$, $CH_2$-O-N ($CH_3$)-$CH_2$, $CH_2$-N($CH_3$) -N($CH_3$) -$CH_2$ and O-N($CH_3$) -$CH_2$-$CH_2$ backbones (where phosphodiester is O-P-O-$CH_2$). Also preferred are oligonucleotides having morpholino backbone structures. Summerton, J. E. and Weller, D. D., U.S. Pat. No. 5,034,506. In other preferred embodiments, such as the protein-nucleic acid or peptide-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, Science 1991, 254, 1497. Other preferred oligonucleotides may contain alkyl and halogen-substituted sugar moieties comprising one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a cholesteryl group; a folate group; a reporter group; an intercalator; a group for improving the pharmacokinetic properties of an oligonucleotide; or a group for improving the pharmacodynamic properties of an oligonucleotide and other substituents having similar properties. Folate, cholesterol or other groups which facilitate oligonucleotide uptake, such as lipid analogs, may be conjugated directly or via a linker at the 2' position of any nucleoside or at the 3' or 5' position of the 3'-terminal or 5'-terminal nucleoside, respectively. One or more such conjugates may be used. Oligonucleotides may also have sugar mimetics such as cyclobutyls in place of the pentofuranosyl group. Other preferred embodiments may include at least one modified base form or "universal base" such as inosine.

The oligonucleotides in accordance with this invention preferably are from about 8 to about 50 nucleotides in length. In the context of this invention it is understood that this encompasses non-naturally occurring oligomers as hereinbefore described, having 8 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as the phosphorothioates and alkylated derivatives. It is also well known to use similar techniques and commercially available modified amidites and controlled-pore glass (CPG) products such as those available from Glen Research, Sterling VA, to synthesize modified oligonucleotides such as cholesterol-modified oligonucleotides.

Methods of inhibiting HBV replication are provided, in which the virus, or cells, tissues or bodily fluid suspected of containing the virus, is contacted with an oligonucleotide of the invention. In the context of this invention, to "contact" means to add the oligonucleotide to a preparation of the virus, or vice versa, or to add the oligonucleotide to a biological sample, or vice versa, or to add the oligonucleotide to virus, cells tissues or bodily fluid in situ, i.e., in an animal. In the context of this invention a "biological sample" is a preparation or isolate of cells or tissues (such as a biopsy sample) or a bodily fluid, for example, blood, urine, sputum or feces.

For prophylactics and therapeutics, methods of preventing HBV-associated disease and of treating HBV infection and HBV-associated disease are provided. The formulation of therapeutic compositions and their subsequent administration is believed to be within the skill in the art. Oligonucleotides may be formulated in a pharmaceutical composition, which may include carriers, thickeners, diluents, buffers, preservatives, surface active agents, liposomes or lipid formulations and the like in addition to the oligonucleotide. Pharmaceutical compositions may also include one or more active ingredients such as antimicrobial agents, anti-inflammatory agents, anesthetics, and the like. Formulations for parenteral administration may include sterile aqueous solutions which may also contain buffers, liposomes, diluents and other suitable additives.

The pharmaceutical composition may be administered in a number of ways depending on whether local or systemic treatment is desired, and on the area to be treated. Administration may be topical (including ophthalmic, vaginal, rectal, intranasal), oral, by inhalation, or parenteral, for example by intravenous drip, subcutaneous, intraperitoneal or intramuscular injection.

Dosing is dependent on severity and responsiveness of the condition to be treated, with course of treatment lasting from several days to several months or until a reduction in viral titer (routinely measured by ELISA, PCR, or DNA blot, for example) is effected or a diminution of disease state is achieved. Optimal dosing schedules are routinely calculated from measurements of drug accumulation in the body. Persons of ordinary skill can easily and routinely determine optimum dosages, dosing methodologies and repetition rates. Therapeutically or prophylactically effective amounts (dosages) may vary depending on the relative potency of individual compositions, and can generally be routinely calculated based on molecular weight and EC50s in in vitro and/or animal studies. For example, given the molecular weight of compound (derived from oligonucleotide sequence and chemical structure) and an effective dose such as an IC50, for example (derived experimentally), a dose in mg/kg is routinely calculated. In general, dosage is from 0.001 µg to 100 g and may be administered once or several times daily, weekly, monthly or yearly, or even every 2 to 20 years.

Pharmacokinetics of antisense oligonucleotides

Because the primary pathology associated with HBV replication occurs in the liver of infected individuals, the ability of a potential anti-HBV compound to achieve significant concentrations in the liver is advantageous. Pharmacokinetic profiles for a number of oligonucleotides, primarily phosphorothioate oligonucleotides, have been determined. Phosphorothioate oligonucleotides have been shown to have very similar pharmacokinetics and tissue distribution, regardless of sequence. In plasma this is seen as a rapid distribution phase (approximately 30 minutes) and a prolonged elimination phase (approximately 40 hours). Phosphorothioates are found to be broadly distributed to peripheral tissues (i.e., excepting the brain, which is reachable directly, e.g., by intraventricular drug administration), with the highest concentrations found in liver, renal cortex and bone marrow. Intact compound has been shown to accumulate in most tissues, particularly liver, kidney and bone marrow, with extended compound half-life in tissues. Studies in mice using a 27-base phosphorothioate oligonucleotide indicated that greater than 40% of bioavailable compound resulting from a single, intravenous dose can be isolated from the liver at 12 hours after injection. Similar distribution profiles are found whether the oligonucleotide is administered intravenously or subcutaneously. Furthermore, the pharmacokinetic and tissue distribution profiles are very consistent among animal species, including rodents, monkeys and humans.

In vitro evaluation of HBV antisense oligonucleotides

A standardized human hepatoblastoma cell culture assay was used for the evaluation of compounds for inhibition of HBV replication. Toxicity of compounds can also be assessed under the same culture and treatment conditions. Korba and Gerin, *Antiviral Res.* 1992, 19, 55–70; Korba and Milman, *Antiviral Res.* 1991, 15, 217–228. This assay is used by the National Institute of Allergy and Infectious Disease (NIAID) to screen drug candidates for treating hepatitis B infection.

The oligonucleotides shown in Table 1 were designed and synthesized as phosphorothioates. Some of these oligonucleotides were tested in this in vitro assay and an EC90 (oligonucleotide concentration (given in micromolar) which gives 90% reduction of HBV DNA levels) was calculated for each oligonucleotide tested. When an oligonucleotide was tested twice, both EC90s are given.

TABLE 1

Antisense oligonucleotides targeted to HBV

| Oligo # | Target | Sequence | Seq. ID | EC90 (μM) |
|---|---|---|---|---|
| 5808 | S-ATG | CCTGATGTGATGTTCTCCATG | 1 | 8.8 ± 0.9 |
| 5812 | S-5'UTR | GAACTGGAGCCACCAGCAGG | 2 | >10 |
| 5813 | preS1-ATG | GAAAGATTCGTCCCCATGC | 3 | 12 ± 1.4 |
| 5814 | preS2-ATG | CCACTGCATGGCCTGAGGATG | 4 | >10 |
| 5815 | C/pregenome-5'cap | TAGGCAGAGGTGAAAAAGTTG | 5 | >10 |
| 5816 | ε/C-5'UT | ACAGCTTGGAGGCTTGAACAG | 6 | >10 |
| 5821 | C-5'UT/ ATG | CCAAAGCCACCCAAGGCACAG | 7 | >10 |
| 5822 | C-5' ATG | ATGTCCATGCCCCAAAGCCAC | 8 | >10 |
| 5823 | P-ATG-L | GATAGGGGCATTTGGTGGTCT | 9 | >10 |
| 5826 | preS1 5'UT | GTTCCCAAGAATATGGTGACC | 10 | >10 |
| 5827 | P-ATG-R | CGGAAGTGTTGATAAGATAGG | 11 | >10 |
| 9586 | ε | TGAACAGTAGGACATGAACA | 12 | 18 |
| 9587 | ε | GGCTTGAACAGTAGGACATG | 13 | 20 |
| 9588 | ε/U5 | TTGGAGGCTTGAACAGTAGG | 14 | 5.9 |
| 9589 | ε/U5 | ACAGCTTGGAGGCTTGAACA | 15 | 3.1, 4.4 |
| 9590 | ε/U5 | AAGGCACAGCTTGGAGGCTT | 16 | 12.1 |
| 9591 | ε/U5 | CACCCAAGGCACAGCTTGGA | 17 | 0.4, 1.3 |
| 9592 | ε/U5 | AAAGCCACCCAAGGCACAGC | 18 | 3.6 |
| 9593 | ε/U5 | GCCCCAAAGCCACCCAAGGC | 19 | 1.3 |
| 9594 | ε/U5 | TCCATGCCCCAAAGCCACCC | 20 | 3.1 |
| 10602 | ε/U5 | GGAGGCTTGAACAGTAGG | 21 | 7.6 |
| 10603 | ε/U5 | CTTGGAGGCTTGAACAGT | 22 | 8.3 |
| 10604 | ε/U5 | CAGCTTGGAGGCTTGAAC | 23 | 7.8 |
| 10605 | ε/U5 | GCACAGCTTGGAGGCTTG | 24 | 5.4 |
| 10606 | ε/U5 | AGGCACAGCTTGGAGGCT | 25 | >10 |
| 10607 | ε/U5 | CCAAGGCACAGCTTGGAG | 26 | 6.5 |
| 10608 | ε/U5 | CACCCAAGGCACAGCTTG | 27 | 6.2 |
| 10609 | ε/U5 | AGCCACCCAAGGCACAGC | 28 | 5.1 |

TABLE 1-continued

Antisense oligonucleotides targeted to HBV

| Oligo # | Target | Sequence | Seq. ID | EC90 (µM) |
|---|---|---|---|---|
| 10610 | ε/U5 | AGGCTTGAACAGTAGG | 29 | >10 |
| 10611 | ε/U5 | TGGAGGCTTGAACAGT | 30 | >10 |
| 10612 | ε/U5 | GCTTGGAGGCTTGAAC | 31 | >10 |
| 10613 | ε/U5 | ACAGCTTGGAGGCTTG | 32 | >10 |
| 10614 | ε/U5 | GCACAGCTTGGAGGCT | 33 | >10 |
| 10615 | ε/U5 | AAGGCACAGCTTGGAG | 34 | >10 |
| 10616 | ε/U5 | CCCAAGGCACAGCTTG | 35 | >10 |
| 10617 | ε/U5 | CCACCCAAGGCACAGC | 36 | >10 |
| 10618 | ε/U5 | AAGCCACCCAAGGCAC | 37 | >10 |
| 10618 | ε/U5 | GCCACGTACACTGACAGCGA | 38 | |
| 11637 | ε/U5 | CATCCAAGGCACAGCTTGGA | 39 | |
| 11638 | ε/U5 | AAAGCCATCCAAGGCA | 40 | |

Of the oligonucleotides tested to date, oligonucleotide numbers 5808, 9588, 9589, 9591, 9592, 9593, 9594, 10602, 10603, 10604, 10605, 10607, 10608, and 10609 have EC90's below 10 µM and are presently preferred. Of these, oligonucleotides 9589, 9591, 9593 and 9594 (SEQ ID NOs: 15, 17, 19 and 20) are presently more preferred.

Animal models for HBV

Woodchuck model

The woodchuck model has been used in hepatitis research for over a decade. Gerin, J. L. 1984. In *Advances in Hepatitis Research*. F. Chisari, ed. Masson Publishing USA, Inc. New York, pp. 40–48; Gerin et al. 1986 In *Vaccines 86: New approaches to Immunization.* F. Brown et al., eds. Cold Spring Harbor Laboratory Press, N.Y., pg 383–386. The woodchuck hepatitis virus (WHV) is closely related to HBV, both immunologically and in terms of sequence homology. Woodchucks are now bred and reared for experimental hepatitis research. Infection of young animals with defined WHV inocula yields chronic carriers for drug testing and research. At least one commercial testing facility is devoted to testing of compounds in woodchucks. Tennant, B. C. and J. L. Gerin. 1994. In *The Liver: Biology and Pathobiology, Third Edition.* I. M. Arias et al., eds. Raven Press, Ltd., N.Y. pp 1455–1466. Because of the sequence homology between HBV and WHV, the efficacy of the oligonucleotides designed and shown in Table 1 can be evaluated in the woodchuck model. Furthermore, demonstration of compound efficacy in this model is a clear demonstration of a specific pharmacologic effect to those of skill in the art.

Chimpanzee model

Chimpanzees are hosts for HBV, and therefore constitute an animal model for HBV induced disease. The serological events following infection in chimpanzees are identical to that observed in humans. Both acute and chronic infections result from exposure of chimpanzees to HBV. However, chimpanzees do not have recognizable clinical symptoms of hepatitis. Cornelius, C. E., 1988, in *The Liver: Biology and Pathobiology,* Second Ed. I. M. Arias et al., eds. Raven Press, Ltd., N.Y., pp. 1315–1336. Demonstration of activity in this model, in which the animal is infected with the same virus that infects humans, is indicative of potential therapeutic effect in humans to those skilled in the art.

Transgenic rat model

A model has very recently been developed using transgenic rats which express human hepatitis B virus genes. Takahashi et al., *Proc. Natl. Acad. Sci. U.S.A.* 1995, 92, 1470–1474. These animals develop acute hepatitis and viral particles and HBeAg are seen in the blood between three and seven days after transfection. HBV is expressed in the liver and liver cell death results. These effects and the subsequent clearing of virions from the blood mimic the effects of acute HBV infection in humans. Therefore activity of compounds in this model is indicative of therapeutic activity in humans to those of skill in the art.

The following examples are provided for illustrative purposes only and are not intended to limit the invention.

EXAMPLES

Example 1

Synthesis and characterization of oligonucleotides

Phosphorothioate deoxyoligonucleotides were synthesized on an automated DNA synthesizer (Applied Biosystems model 380B) using standard phosphoramidite chemistry. The standard oxidation bottle was replaced by a 0.2 M solution of 3H-1,2-benzodithiole-3-one 1,1-dioxide in acetonitrile for the stepwise thiation of the phosphite linkages. The thiation cycle wait step was increased to 68 seconds and was followed by the capping step. β-cyanoethyldiisopropyl-phosphoramidites were purchased from Applied Biosystems (Foster City, Calif.).

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0. Oligodeoxynucleotides and phosphorothioate oligonucleotides were judged from electrophoresis to be greater than 80% full length material.

Example 2

In vitro analysis of oligonucleotide inhibition of HBV replication

Oligonucleotides were evaluated in a standardized cell culture assay. Korba and Gerin, *Antiviral Res.* 1992, 19, 55–70; Korba and Milman, *Antiviral Res.* 1991, 15, 217–228. Briefly, human hepatoblastoma 2.2.15 cells were grown as described by Korba and Milman, ibid. Confluent cultures in 24-well plates were treated with 10 consecutive daily doses of 0.3 $\mu$M, 1 $\mu$M, 3 $\mu$M or 10 $\mu$M oligonucleotide in RPMI1640 medium with 2% fetal bovine serum. Medium was assayed for HBV virion DNA before treatment and periodically during treatment. Intracellular HBV DNA was analyzed after 10 days of treatment. HBV DNA was extracted from medium and analyzed by slot blot analysis. Cellular DNA was prepared and analyzed by Southern blot analysis (Korba and Milman, ibid) using a $^{32}$P-labelled 3.2 kb EcoRI HBV DNA fragment as probe. Quantitation was by comparison to HBV standards loaded on each gel.

Toxicity was determined by inhibition of neutral red dye uptake in cells grown in 96-well plates and treated as described above. One day after the final addition of compound, medium was removed and 0.2 ml of DPBS containing 0.01% neutral red dye (Sigma, Inc.) was added to each well. Cells were allowed to recover for two hours. Dye was removed, cells were washed with DPBS and then 0.2 ml of 50% EtOH/1% glacial acetic acid was added to each well. After 30 minutes of gentle mixing, absorbance at 510 nm was measured and compared to untreated control cultures. $CC_{50}$ (50% cytotoxic concentration) values were calculated.

Example 3

Testing of oligonucleotides in woodchucks

Oligonucleotides are evaluated at Marmotech, Inc. (Ithaca, N.Y.), a commercial facility which routinely screens anti-HBV and anti-hepatocellular carcinoma drug candidates in the woodchuck hepatitis model. Gerin, J. L. 1984. In *Advances in Hepatitis Research.* F. Chisari, ed. Masson Publishing USA, Inc. New York, pp. 40–48; Gerin et al. 1986 In *Vaccines 86: New approaches to Immunization.* F. Brown et al., eds. Cold Spring Harbor Laboratory Press, N.Y., pg 383–386. Two doses of oligonucleotides are tested, 20 mg/kg and 2 mg/kg, with three animals receiving each dose. Oligonucleotides are administered intravenously in 0.1 ml of PBS every other day for 30 days, for a total of 15 doses. The primary end point of the assay is level of circulating virus. Blood samples are collected on day 0, prior to drug treatment, and at days 1, 2, 4, 8, 15, 22 and 30 of treatment. Virus is quantitated by dot blot or Southern blot analysis using standard methods (Sambrook et al., 1989, *Molecular Cloning: A Laboratory Manual,* Cold Spring Harbor, N.Y.).

Example 4

Testing of oligonucleotides in transgenic rats

A cloned HBV homodimer construct is prepared and delivered into partially hepatectomized Sprague-Dawley rats as described in Takahashi et al., *Proc. Natl. Acad. Sci. U.S.A.* 1995, 92, 1470–1474. HBV constructs are directly delivered into livers by complexing the constructs with the cationic lipid dioctadecylamidoglycylspermine and injecting the mixture into the right median lobe of the liver while the portal veins are temporarily ligated. Takahashi et al., ibid. To determine that transfection has occurred, HBV RNA is detected in rat tissues by RT-PCR, HBV virion is detected in rat serum by immunoprecipitation and PCR, HBV DNA is detected in rat liver by Southern blotting and HBeAg and anti-HBe antibody can be detected in rat sera by ELISA. Takahashi et al., ibid.

Oligonucleotides are administered in 0.1 ml PBS by intravenous injection into the tail vein other day for 30 days. 2 mg/kg and 20 mg/kg doses are used. Effects of antisense inhibition of HBV are determined by detection of HBV RNA, DNA, virion, HBeAg and anti-HBe antibody as above.

Example 5

Diagnostic use of oligonucleotides which inhibit HBV replication

Definitive diagnosis of HBV-caused hepatitis can be readily accomplished using antisense oligonucleotides which inhibit HBV replication. DNA is extracted from blood samples or liver tissue samples obtained by needle biopsy, and electrophoresed and transferred to nitrocellulose for Southern blotting, or transferred directly to nitrocellulose for dot blot analysis according to standard methods (Current Protocols in *Molecular Biology,* Frederick M. Ausubel et al., eds., John Wiley & Sons Inc., 1994, Section 2.9B). HBV DNA is quantitated using an appropriate DNA probe which hybridizes to HBV DNA. An identical sample of blood or tissue is treated with antisense oligonucleotide at an appropriate concentration (determined from $EC_{90}$ as hereinbefore stated) to inhibit HBV replication prior to DNA extraction and blotting. The intensity of putative HEV signal in the two blots is then compared. If replicating HBV is present (and presumably causative of disease), the HBV signal will be reduced in the oligonucleotide-treated sample compared to the untreated sample, due to inhibition of HBV replication by the oligonucleotide. If HBV infection (replicating HBV) is not present, the two samples will have identical signals. Similar assays can be designed which employ other methods such as PCR, RT-PCR or Northern blotting, all of which are routinely performed by those in the art.

Diagnostic methods using antisense oligonucleotides capable of inhibiting HBV replication are also useful for determining whether a given virus isolated from a patient with hepatitis will respond to treatment, before such treatment is initiated. DNA is isolated from a patient's blood or a liver tissue sample and blotted as described above. An identical sample of blood or tissue is treated with antisense oligonucleotide to inhibit HBV replication prior to DNA extraction and blotting. The intensity of putative HBV signal in the two blots is then compared. If the oligonucleotide is capable of inhibiting replication of the patient-derived virus, the HBV signal will be reduced in the oligonucleotide-treated sample compared to the untreated sample. This indicates that the patient's HBV infection is responsive to treatment with the antisense oligonucleotide, and a course of therapeutic treatment can be initiated. If the two samples have identical signals the oligonucleotide is not able to inhibit replication of the virus, and another method of treatment is indicated. Similar assays can be designed which employ other methods such as PCR, RT-PCR or Northern blotting, all of which are routinely performed by those in the art.

What is claimed:

1. A method of inhibiting hepatitis B virus replication in vitro comprising incubating hepatitis B virus or incubating cells, tissues, or a bodily fluid which contains hepatitis B virus with an antisense oligonucleotide, wherein the sequence of said antisense oligonucleotide consists of SEQ.ID.NO: 1, 14, 15, 17, 18, 19, 20, 21, 22, 23, 24, 26, 27, or 28, under conditions where viral replication is inhibited.

2. An antisense oligonucleotide which inhibits hepatitis B virus replication, wherein the sequence of said antisense oligonucleotide consists of SEQ. ID. NO: 1, 14, 15, 17, 18, 19, 20, 21, 22, 23, 24, 26, 27, or 28.

* * * * *

UNITED STATES PATENT AND TRADEMARK OFFICE
CERTIFICATE OF CORRECTION

PATENT NO. : 5,985,662
DATED : November 16, 1999
INVENTOR(S) : Anderson et al.

It is certified that error appears in the above-identified patent and that said Letters Patent is hereby corrected as shown below:

Column 1,
Line 25, please delete "interferon-a" and insert -- interferon-α --.

Column 3,
Line 23, please delete "E" and insert -- ϵ --.

Column 5,
Line 19, please delete "E" and insert -- ϵ --.
Line 48, please delete "E" and insert -- ϵ --.
Line 60, please delete "modulationt" " and insert -- "modulation " --.

Signed and Sealed this

Fourth Day of June, 2002

Attest:

JAMES E. ROGAN
Attesting Officer  Director of the United States Patent and Trademark Office